US009220641B2

(12) United States Patent
Carbonari

(10) Patent No.: US 9,220,641 B2
(45) Date of Patent: Dec. 29, 2015

(54) DISPOSABLE ABSORBENT PRODUCT WITH BONDED LATERAL REGIONS AND RELATED METHODS

(75) Inventor: Raquel Carbonari, Philadelphia, PA (US)

(73) Assignee: SCA HYGIENE PRODUCTS AB, Göteborg (SE)

( * ) Notice: Subject to any disclaimer, the term of this patent is extended or adjusted under 35 U.S.C. 154(b) by 849 days.

(21) Appl. No.: 13/334,579

(22) Filed: Dec. 22, 2011

(65) Prior Publication Data

US 2013/0165896 A1 Jun. 27, 2013

(51) Int. Cl.
A61F 13/15 (2006.01)
A61F 13/20 (2006.01)
A61F 13/475 (2006.01)
A61F 13/494 (2006.01)
A61F 13/515 (2006.01)

(52) U.S. Cl.
CPC ....... *A61F 13/4757* (2013.01); *A61F 13/15747* (2013.01); *A61F 13/4752* (2013.01); *A61F 13/49413* (2013.01); *A61F 13/515* (2013.01); *Y10T 156/1049* (2015.01)

(58) Field of Classification Search
CPC ............ A61F 13/515; A61F 13/55115; A61F 2013/49023; A61F 13/15747; A61F 13/539; A61F 13/4757; A61F 5/485; B31F 1/0029; B32B 27/12; D04H 1/5405
USPC ..................... 604/378, 380, 385.101, 385.01, 604/385.201; 450/57, 63, 68–69
See application file for complete search history.

(56) References Cited

U.S. PATENT DOCUMENTS

| | | | |
|---|---|---|---|
| 4,505,705 A | 3/1985 | Matthews et al. | |
| 4,579,556 A | 4/1986 | McFarland | |
| 5,181,563 A | 1/1993 | Amaral | |

(Continued)

FOREIGN PATENT DOCUMENTS

| | | |
|---|---|---|
| EP | 1133963 | 9/2001 |
| GB | 1461908 A | 1/1977 |

(Continued)

OTHER PUBLICATIONS

International Search Report and Written Opinion mailed Jan. 28, 2013, issued in International Patent Application No. PCT/EP2012/071361, filed Oct. 29, 2012.

(Continued)

*Primary Examiner* — Michele M Kidwell
(74) *Attorney, Agent, or Firm* — Drinker Biddle & Reath LLP

(57) ABSTRACT

A disposable absorbent product extends along a longitudinal axis and a transverse axis orthogonal to the longitudinal axis. The product has a topsheet, and a backsheet overlaying the topsheet, with the topsheet and backsheet jointly defining first and second side edges of the product on respective sides of the longitudinal axis. An absorbent core is disposed between the topsheet and the backsheet for storing fluid secreted by the wearer of the product. The absorbent core has first and second lateral edges respectively inboard of the first and second side edges of the product so as to define respective first and second lateral portions of the product that are free of the absorbent core. The product also has a plurality of folds parallel to the transverse axis, and a plurality of bonds in at least one of the first or second lateral portions that secure the plurality of folds in place.

20 Claims, 5 Drawing Sheets

(56) References Cited

U.S. PATENT DOCUMENTS

| | | | |
|---|---|---|---|
| 5,611,790 A | | 3/1997 | Osborn, III et al. |
| 5,993,431 A | * | 11/1999 | McFall et al. ............ 604/385.24 |
| 6,500,159 B1 | * | 12/2002 | Carvalho ................. 604/385.01 |
| 7,156,831 B2 | | 1/2007 | Otsubo |
| 7,252,656 B2 | * | 8/2007 | Bonelli et al. ........... 604/385.04 |
| 7,368,027 B2 | | 5/2008 | Schneider et al. |
| 2004/0167490 A1 | * | 8/2004 | Nelson et al. ............ 604/385.01 |
| 2005/0155888 A1 | * | 7/2005 | Osterdahl et al. ............. 206/494 |
| 2005/0165377 A1 | * | 7/2005 | Klitzke et al. ........... 604/385.01 |
| 2010/0298803 A1 | * | 11/2010 | Popp et al. ............... 604/385.23 |
| 2011/0017628 A1 | * | 1/2011 | Oba et al. ...................... 206/494 |

FOREIGN PATENT DOCUMENTS

| | | | | |
|---|---|---|---|---|
| GB | 2 296 445 | * | 7/1996 | ............. A61F 13/15 |
| WO | WO-9613237 A1 | | 5/1996 | |

OTHER PUBLICATIONS

Internet site: http://beautyandthebump.blogspot.com/2011/08/review-lansinoh-nursing-pads-vs-medela.html#.TuuODFaD18E.
Internet site: http://gotbreastpump.com/store/Lansinoh_disposable_nursing_pads_36.htm.
International Preliminary Search Report dated Jun. 24, 2014, issued in International Patent Application No. PCT/EP2012/071361, filed Oct. 29, 2012.

* cited by examiner

DISPOSABLE ABSORBENT PRODUCT WITH BONDED LATERAL REGIONS AND RELATED METHODS

TECHNICAL FIELD

The present invention is generally related to absorbent products and, more particularly, to disposable absorbent products that are worn by humans for the containment and absorption of fluid bodily secretions.

BACKGROUND

Disposable absorbent products for absorption of bodily fluids are available in different types, designs, and dimensions. For example, training pants, baby diapers, adult diapers, and incontinence guards are products designed for the containment of urine and excrement. There are other types of disposable absorbent articles, such as feminine hygiene products (e.g., heavy and light incontinence pads, pantiliners) that are designed to contain and absorb urine and/or menses secreted by female wearers. Known products of this type typically include a topsheet facing the body of the wearer, a backsheet facing the garment worn by the wearer, and an absorbent core sandwiched between the topsheet and backsheet.

There are known disposable absorbent products, such as pantiliners and the like, that a generally flat configuration i.e., shape, during use. This flat configuration may limit the ability of the product to contain fluids secreted by the wearer of the product. Yet other conventional disposable absorbent products, such as diapers, rely on leg elastics and/or elasticized standing leg barriers to attain a shape that enhances containment of fluids secreted by the wearer. The addition of leg elastics and/or elasticized standing leg barriers, however, adds to the complexity and cost in the manufacturing of disposable absorbent products of those types.

Accordingly, it is desirable to provide disposable absorbent products that address these and other shortcomings of conventional disposable absorbent products.

SUMMARY

In one embodiment, a disposable absorbent product is provided that extends along a longitudinal axis and a transverse axis orthogonal to the longitudinal axis. The disposable absorbent product has a topsheet, and a backsheet overlaying the topsheet, with the topsheet and backsheet jointly defining first and second side edges of the disposable absorbent product on respective sides of the longitudinal axis. An absorbent core is disposed between the topsheet and the backsheet for storing fluid secreted by the wearer of the disposable absorbent product.

The absorbent core has first and second lateral edges respectively inboard of the first and second side edges of the disposable absorbent product so as to define respective first and second lateral portions of the disposable absorbent product that are free of the absorbent core. The disposable absorbent product also has a plurality of folds parallel to the transverse axis, and a plurality of bonds in at least one of the first or second lateral portions that secure the plurality of folds in place.

In specific embodiments, the bonds do not extend to the absorbent core. Yet in other embodiments, at least two of the bonds are located along a common transverse line in the first and second lateral portions. In specific embodiments, the first and second lateral edges of the absorbent core define a plurality of lateral depressions of the absorbent core at the folds. The bonds may be, for example, adhesive bonds, ultrasonic bonds, infrared bonds, thermal bonds, compression bonds, or any combination thereof. The lateral portions may be free of elastic strands. Additionally or alternatively, the disposable absorbent product may be in the form of a diaper, with the diaper being free of standing leg barriers.

In another embodiment, a disposable absorbent product is provided that extends along a longitudinal axis and a transverse axis orthogonal to the longitudinal axis. The disposable absorbent product has a topsheet and a backsheet overlaying the topsheet, with the topsheet and backsheet jointly defining first and second side edges of the disposable absorbent product on respective sides of the longitudinal axis. An absorbent core is disposed between the topsheet and the backsheet for storing fluid secreted by the wearer of the disposable absorbent product. The absorbent core has first and second lateral edges respectively inboard of the first and second side edges of the disposable absorbent product so as to define respective first and second lateral portions of the disposable absorbent product that are free of the absorbent core. The disposable absorbent product also has a plurality of folds parallel to the transverse axis, and a plurality of bonds located along the folds and spanning the first and second lateral portions, with the bonds securing the plurality of folds in place.

Yet in another embodiment, a method is provided for making a disposable absorbent product that includes a topsheet, a backsheet, and an absorbent core disposed between the topsheet and backsheet, and in which the topsheet and backsheet jointly define first and second side edges of the disposable absorbent product on respective sides of a longitudinal axis of the disposable absorbent product. The method includes locating the absorbent core relative to the topsheet and backsheet so as to define respective first and second lateral portions of the disposable absorbent product that are free of the absorbent core. The method also includes forming a plurality of folds parallel to a transverse axis of the disposable absorbent product that is orthogonal to the longitudinal axis thereof.

At least one of the first or second lateral portions is bonded at a plurality of the folds, so as to secure the folds in place. The bonding of the at least one of the first or second lateral portions may include leaving the absorbent core free of bonds. Additionally or alternatively, bonding of the at least one of the first or second lateral portions may include forming an adhesive, ultrasonic, infrared, thermal, or compression bond at the first or second lateral portion. In specific embodiments, the method includes forming at least one fold spanning the first and second lateral portions and extending along a common line parallel to the transverse axis, and bonding the first and second lateral portions along the at least one fold.

BRIEF DESCRIPTION OF THE DRAWINGS

The objectives and features of the invention will become more readily apparent from the following detailed description taken in conjunction with the accompanying drawings in which.

DETAILED DESCRIPTION

Figure 1:
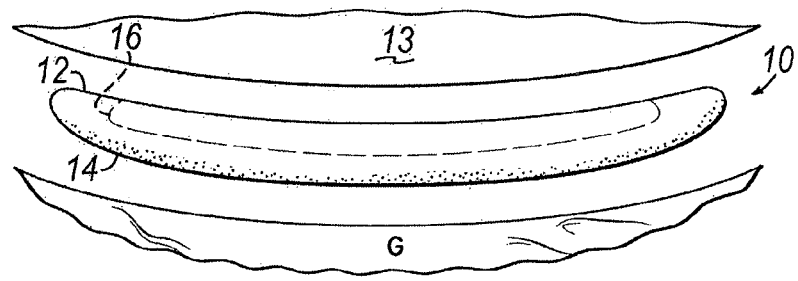
FIG. 1 is a perspective view of a disposable absorbent product in accordance with one embodiment of the invention.
Figure 2:
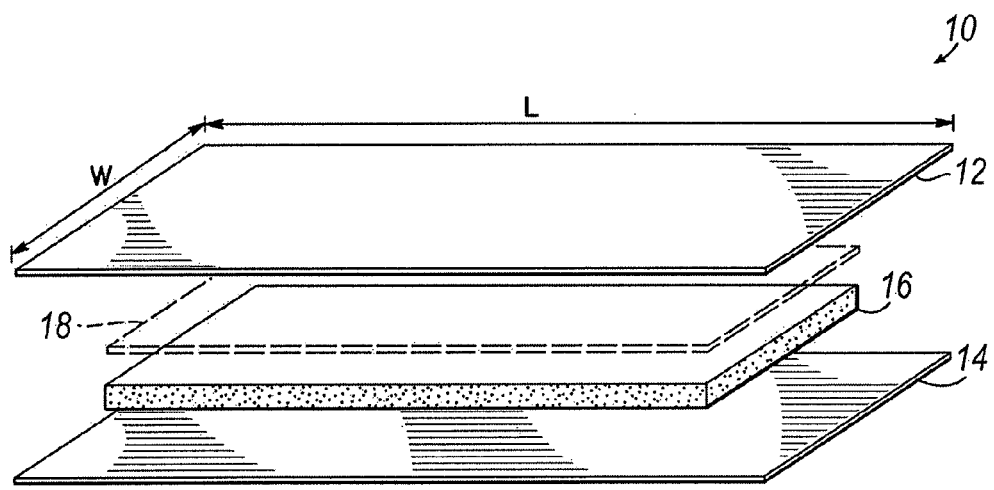
FIG. 2 is a schematic disassembled view of the product of FIG. 1.

With reference to the figures, and more particularly to FIGS. 1 and 2, an exemplary disposable absorbent product in the form of an incontinence pad 10 is illustrated. While these and other figures refer to an incontinence pad, it is contemplated that the description herein and accompanying figures are applicable to other types of disposable absorbent products, and therefore not limited to incontinence pads. For example, and without limitation, the various features described herein may be used in baby diapers, adult diapers, training pants, adult-size disposable pads, feminine catamenial pads, or male or female light-incontinence, medium-incontinence, or heavy-incontinence pads.

The exemplary pad 10 includes a topsheet 12, and a backsheet 14 disposed opposite the topsheet 12. When worn, the topsheet 12 faces the body of the wearer, schematically represented and assigned the numeral 13, while the backsheet 14 faces away from the body 13 of the wearer. In the case of known uses of feminine pads and similar products, the backsheet 14 faces a garment G worn by the wearer. While not shown, the feminine pad 10 may include one or more features such as lateral extensions resembling wings, adhesive components, or mechanical entanglement-type (hook-and-loop) fasteners that allow the wearer to secure the pad 10 to the garment G. Additionally or alternatively, and while also not shown, the pad 10 may include adhesive or mechanical components that allow the pad 10 to be secured directly onto the body 13 of the wearer.

The topsheet 12 is made of a permeable, hydrophilic material such as a hydrophilic nonwoven, and may be in the form of a single, continuous layer across the width of the pad 10, or may be in the form of two or more layers of the same material or of materials different from one another that jointly, but not individually, span the length and width of the pad 10. The backsheet 14 is made of an impermeable, hydrophobic material such as a hydrophobic nonwoven or a laminate made of one or more layers of nonwoven material and one or more layers of polypropylene or polyethylene film. Backsheet 14 may be in the form of a single, continuous layer across the length and width of the diaper 10, or may alternatively be in the form of two or more layers of the same material or of materials different from one another that jointly, rather than individually, span the length and width of the diaper 10. The pad 10 also includes an absorbent core 16, disposed between the topsheet 12 and backsheet 14, that is configured to absorb and retain body fluids, such as urine and/or menses, secreted by the wearer.

An optional acquisition layer 18 (FIG. 2) or similar structure may be present that is primarily designed to acquire and/or distribute fluids received through the topsheet 12 and to direct same toward the core 16, which is designed to store fluid, as explained in commonly-assigned U.S. patent application Ser. No. 13/269,292, filed 7 Oct. 2011, entitled "Disposable Absorbent Product with Multiple Fluid Storage Structures and Related Methods," the entire contents of which are hereby expressly incorporated by reference herein. In that regard, it is contemplated that the optional acquisition layer 18 may, in certain embodiments, be free of fluid-storage materials such as superabsorbent material ("SAP") and/or be free of fluff pulp.

Figure 3:
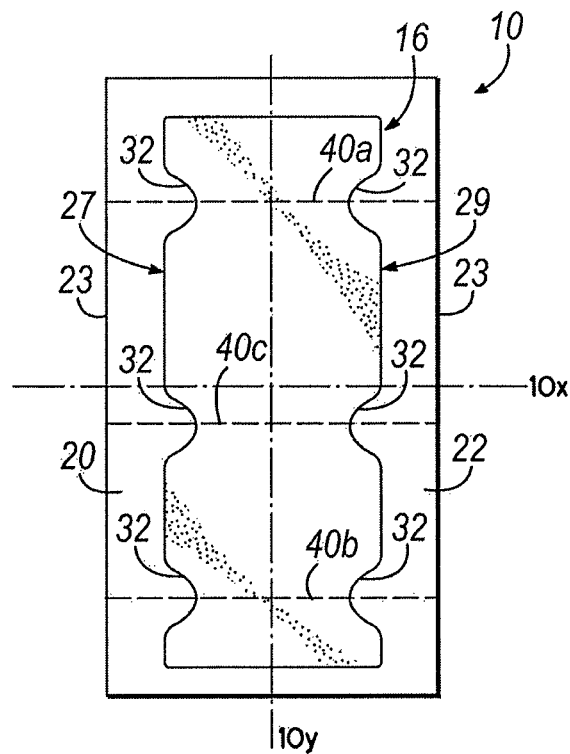
FIG. 3 is a top view of the product of FIGS. 1 and 2.

With continued reference to FIGS. 1-2, and further referring now to FIG. 3, the core 16 and the pad 10 of which core 16 forms part, extend along a longitudinal axis 10y, and along a transverse axis 10x orthogonal to the longitudinal axis 10y. Further, the core 16 has a symmetrical outer profile in the plane defined by the length (longitudinal axis 10y) and width (transverse axis 10x) dimensions of the pad 10, although those of ordinary skill in the art will readily appreciate that such shape is exemplary rather than limiting. For example, and without limitation, the core 16 may instead have any other regular or irregular shape, symmetrical or asymmetrical.

The core 16 is located relative to other portions of the pad 10 so as to define a pair of lateral portions 20, 22 on each side of the longitudinal axis 10y that are free of core 16 i.e., which do not contain any portion of the core 16 therein. More specifically in this embodiment, the lateral position (i.e., along transverse axis 10x) of core 16 is such that the core 16 is substantially centered relative to the rest of the pad 10. It is contemplated, however, that the core 16 may instead be laterally offset, rather than being substantially centered, and still fall within the scope of the present disclosure. In the illustrated embodiment, the core 16 is also longitudinally centered, although this is merely exemplary, insofar as other non-centered relative longitudinal positions of the core 16 are contemplated as well.

The lateral portions 20, 22 are made up of portions of the topsheet 12 and backsheet 14 and, in that regard, may include non-woven materials, polyethylene films, polypropylene films, or combinations thereof, depending on the materials defining the topsheet 12 and backsheet 14. The lateral portions 20, 22 may in some embodiments include portions of other components, such as the optional acquisition layer 18 (FIG. 2) described above, or other components. Further, in some embodiments, either the topsheet 12 or the backsheet 14 may wrap around the other of the topsheet 12 or the backsheet 14 at the lateral portions 20, 22.

The topsheet 12 and backsheet 14 jointly define a pair of lateral or side edges 23 of the pad 10. The core 16 has a perimeter, in the plane defined by the axes 10x,10y, that includes first and second lateral edges 27, 29, both inboard of the lateral edges 23 of pad 10. Further in the illustrated embodiment, the core 16 has a plurality of depressions or notches 32 along the lateral edges 27, 29, although these are exemplary rather than limiting. More specifically, cores 16 are contemplated having no depressions 32 at all, or alternatively having depressions in shapes and/or numbers different from those shown in FIG. 3, and still fall within the scope of the present disclosure.

With continued reference to FIGS. 1-3, pad 10 has a plurality of transverse folds 40a, 40b, 40c that span the entire width of the pad 10 and which are, in this embodiment, generally parallel to the transverse axis 10x. While the exemplary pad 10 of FIGS. 1-3 has a total of three such folds, those of ordinary skill in the art will readily appreciate that the pad 10 may instead have transverse folds 40a, 40b, 40c in a number different from that shown and described herein. Further, the pad 10 may alternatively have folds that do not span the entire width of pad 10, but which, for example, are only present at one or both of the lateral portions 20, 22 i.e., folds which do not extend into the core 16.

Notably in the illustrated embodiment, the location of depressions 32 in the longitudinal dimension (axis 10y) coincides with the longitudinal location of the folds 40a, 40b, 40c. This relative location of the depressions 32 may be desirable to facilitate folding of the pad 10, especially in embodiments in which the entire pad 10, including the core 16, is folded along folds 40a, 40b, 40c, as explained more fully below.

Figure 4A:
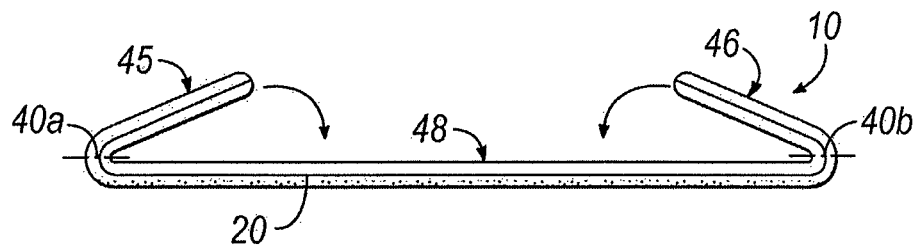
FIG. 4A is an elevation, schematic view of a disposable absorbent product, illustrating one step of a process in accordance with another embodiment of the invention.
Figure 4B:
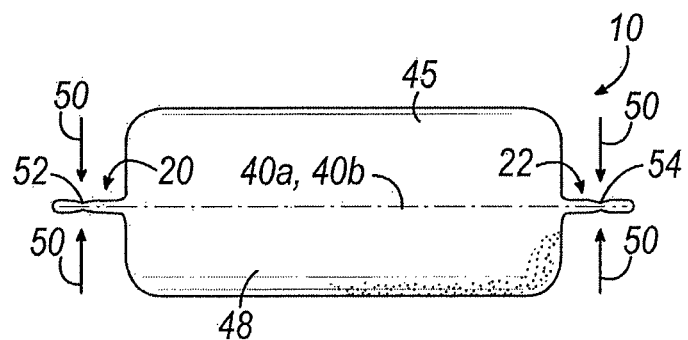
FIG. 4B is a top, schematic view of the exemplary product and process of FIG. 4A.

FIGS. 4A, 4B, 5A, 5B, 6A, and 6B schematically illustrate an exemplary folding process in accordance with one embodiment of the invention. In particular, FIGS. 4A and 4B illustrate the formation of a first pair of transverse folds 40a, 40b, by virtue of the inward folding of two terminal portions 45, 46 of pad 10 relative to a central portion 48. Subsequent to formation of the folds 40a, 40b, a pair of bonds is formed (arrows 50) at the lateral portions 20, 22, so as to secure the folds 40a, 40b in place at the lateral portions 20, 22. The resulting bonds 52, 54 are formed, for example and without limitation, through adhesive bonding, ultrasonic bonding, infrared bonding, compression bonding (e.g., CPW, crimping), thermal bonding, combinations thereof, or any other type of bonding suitably chosen to bond the materials making up lateral portions 20, 22 so as to secure the folds 40a, 40b in place. In the embodiment of FIGS. 4A and 4B, moreover, the bonds 52, 54 are formed in pairs along common lines of folding. More specifically, the bonds 52, 54 are formed such that each bond 52 in lateral portion 20 is in longitudinal registration with one bond 54 in lateral portion 22). This particular configuration is exemplary rather than limiting, insofar one or more bonds in lateral portion 20 may be staggered (in the longitudinal dimension) relative to bonds formed in lateral portion 22.

Figure 5A:
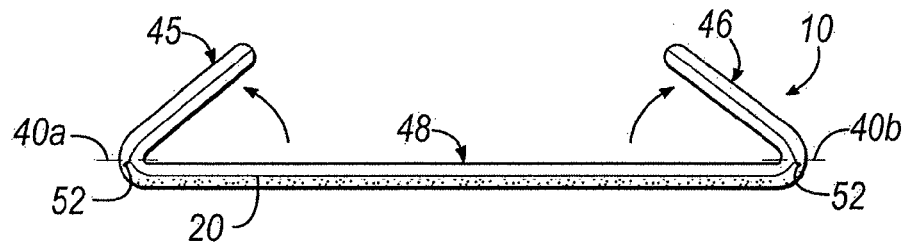
FIG. 5A is an elevation, schematic view of the product of FIGS. 4A, 4B, and 5A, illustrating another step of the exemplary process shown therein.
Figure 5B:
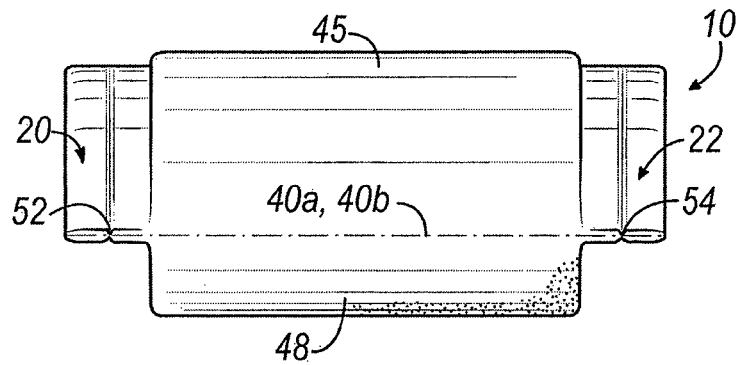
FIG. 5B is a top, schematic view of the exemplary product and process of FIG. 5A.
Figure 6A:
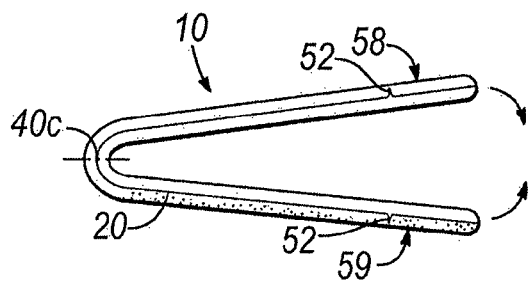
FIG. 6A is an elevation, schematic view of the product of FIGS. 4A, 4B, 5A, and 5B, illustrating yet another step of the process shown in those figures.
Figure 6B:
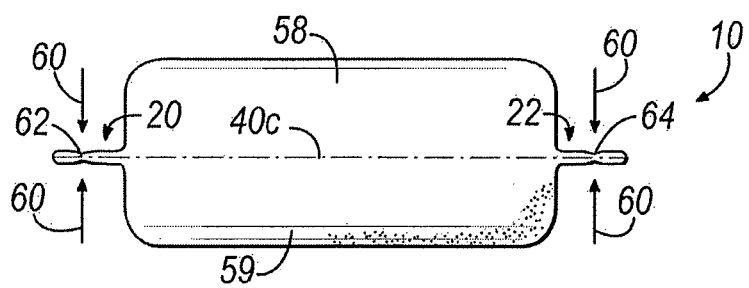
FIG. 6B is a top, schematic view of the exemplary product and process of FIG. 6A.
Figure 7A:
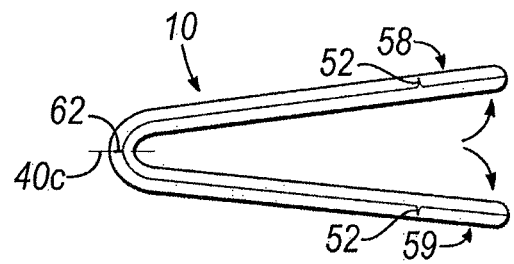
FIG. 7A is an elevation, schematic view of the product of FIGS. 4A, 4B, 5A, 5B, 6A, and 6B illustrating another step of the process shown in those figures.
Figure 7B:
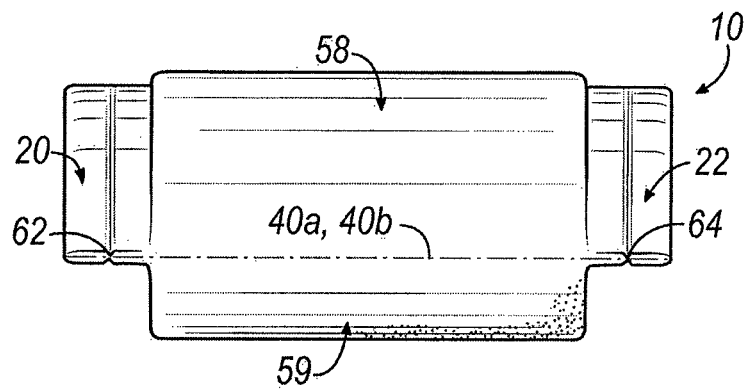
FIG. 7B is a top, schematic view of the exemplary product and process of FIG. 7A.

FIGS. 5A and 5B illustrate the terminal portions 45, 46 being unfolded after formation of the bonds 52, 54. A subsequent fold is illustrated in FIGS. 6A and 6B. Those figures show the formation of a third transverse fold 40c, effected by inwardly folding two terminal portions (e.g., halves) 58, 59 of pad 10 onto one another. Arrows 60 schematically represent the formation of another pair of bonds 62, 64 at the lateral portions 20, 22, respectively, that secure the fold 40c in place at the lateral portions 20, 22. The resulting bonds 62, 64 are formed in ways similar to or different from those described above with respect to the formation of bonds 52, 54 (FIGS. 4A, 4B, 5A, 5B). FIGS. 7A and 7B illustrate subsequent unfolding of the pad 10 along fold 40c.

While the embodiment of FIGS. 4A, 4B, 5A, 5B, 6A, 6B, 7A, and 7B show an exemplary process in which no part of the core 16 is bonded i.e., the bond formation is limited to the lateral portions 20, 22, it is contemplated that at least some portions of the core 16 may instead be bonded along with the bonds being formed in one or both of the lateral portions 20, 22, and still fall within the scope of the present disclosure.

As noted above, and additionally referring again to FIG. 3, the depressions 32 at the lateral edges 27, 29 of core 16 facilitate folding of the pad 10 in embodiments in which the entire pad 10 is folded. In this regard, the exemplary folding illustrated particularly in FIGS. 4A, 4B, 6A, and 6B, in which the entire pad 10 is folded, may create areas of stress concentration in core 16 along the lateral edges 27, 29, at the folds 40a, 40b, 40c. The removal of core 16 material from those lateral edges 27, 29 at the fold locations, which defines the depressions 32, eliminates or at least reduces the stress concentration along the lateral edges 27, 29 at the folds 40a, 40b, 40c. This, in turn, facilitates maintaining the integrity of the core 16 during the folding.

In addition to the above, the depressions 32 also facilitate formation of the bonds 52, 54, 62, 64. More specifically, the depressions 32 increase the area of lateral portions 20, 22 that is available for formation of the bonds 52, 54, 62, 64, which may be desirable in the formation of bonds 52, 54, 62, 64 requiring a minimum width to secure the folds in place e.g., adhesive bonds. The depressions 32 also increase the area available for engagement of bond-forming equipment (e.g., CPW rolls, ultrasonic wheels, ultrasonic horn and anvil, infrared equipment, heat sealers) with the lateral portions 20, 22.

Also, while FIGS. 4A, 4B, 5A, 5B, 6A, 6B, 7A, and 7B describe an exemplary process in which two folds 40a, 40b are formed first, followed by unfolding and then by forming of a third fold 40c, those of ordinary skill in the art will readily appreciate that same is illustrative rather than limiting. More specifically, other types of folds, in any other number, and/or in sequences different from those shown, are contemplated. Also, processes are contemplated in which no unfolding (as shown in FIGS. 5A, 5B) is required prior to the formation of a subsequent additional fold. Yet other processes are contemplated in which only the first two folds 40a, 40b are formed, without a need to form a third fold 40c.

In addition to the above, alternative processes are contemplated in which only the lateral portions 20, 22 are folded, rather than the entire pad 10. More specifically, embodiments are contemplated, for example, in which the folds 40a, 40b, 40c and bonds 52, 54, 62, 64 are formed prior to joining of the core 16 with the topsheet 12 and backsheet 14. In those alternative embodiments, folding of the core 16 is avoided or in some cases reserved for a final fold of the entire pad 10 prior to packaging or the like.

Similarly, other embodiments are contemplated in which only one, rather than both of the lateral portions 20, 22, is folded and/or bonded. In that regard, an exemplary process is contemplated, similar to that illustrated by the sequence of FIGS. 4A, 4B, 5A, 5B, 6A, 6B, 7A, and 7B, but in which bonds 52, 54, 62, 64 are formed only in lateral portion 20 or only in the other lateral portion 22. Yet other processes are contemplated, as discussed above, in which the bonds 52, 62 on the lateral portion 20 are staggered relative to the bonds 54, 64 on the opposite lateral portion 22.

Figure 8:
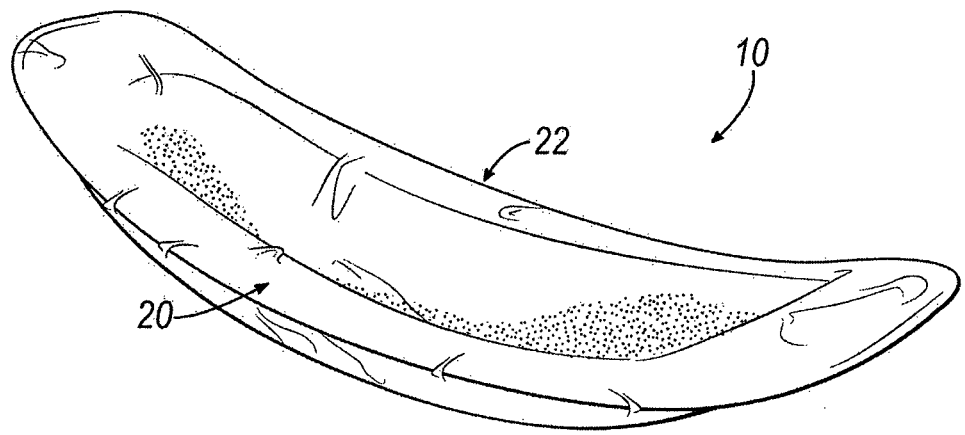
FIG. 8 is a perspective view of a disposable absorbent product in accordance with another embodiment of the invention.

FIG. 8 illustrates an exemplary pad 10 made by the exemplary process illustrated at FIGS. 4A, 4B, 5A, 5B, 6A, 6B, 7A, and 7B. FIG. 8 thus shows a pad 10 in which the folds 40a, 40b, 40c and corresponding bonds 52, 54, 62, 64 effectively gather the lateral portions 20, 22 so as to cause pad 10 to have a cupped configuration. The attained cupped configuration may be desirable because it has been observed to enhance containment of the fluids secreted by the wearer of the pad 10, and also because it has been observed to enhance fit and comfort of pad 10 on the body 13 (FIG. 1) of the wearer.

Figure 9:
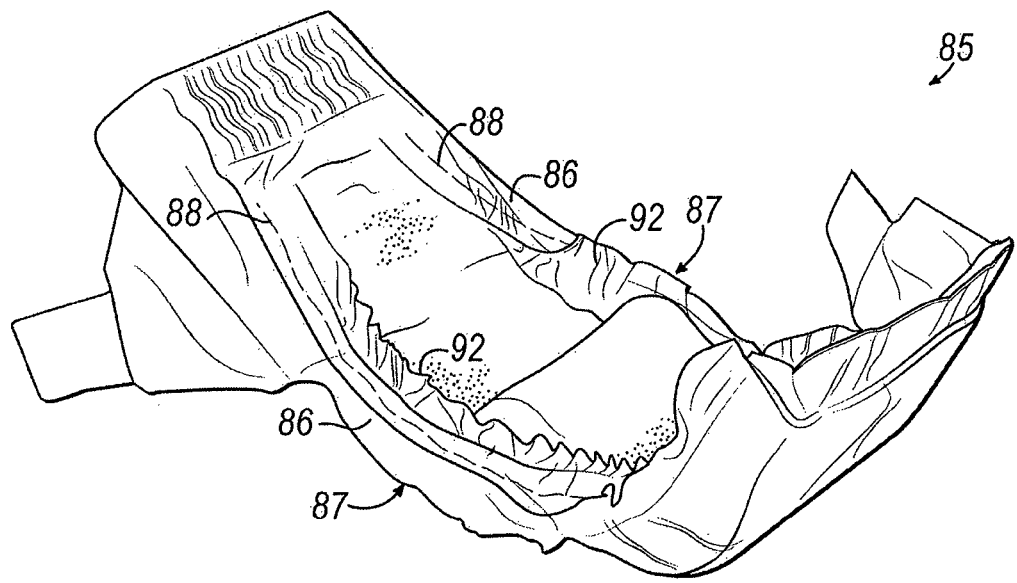
FIG. 9 is a perspective view of a prior art diaper.

FIG. 9 illustrates a conventional, prior art diaper 85. Diaper 85 has a pair of lateral portions 86, partially defining the leg openings 87 of diaper 85. Each of the lateral portions 86 includes one or more elastic strands ("leg elastics") 88 that gather the lateral portions 86 so to facilitate conformance of the diaper 85 around the legs of the wearer. Diaper 85 also includes a pair of cuffs or standing leg barriers 92 that, in use, enhances containment of fluids e.g., urine, secreted by the wearer.

Figure 10:
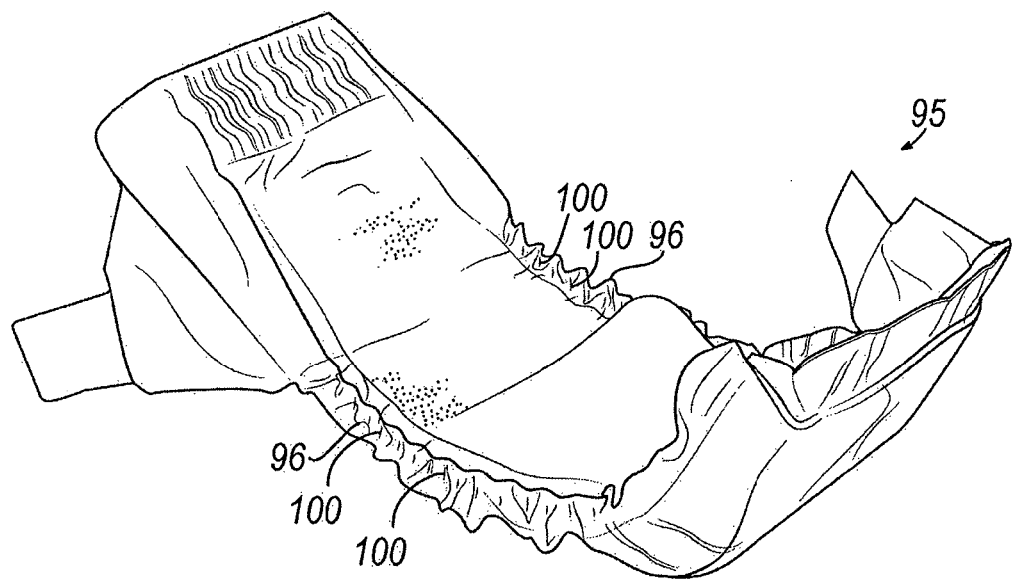
FIG. 10 is a perspective view of a disposable absorbent product in accordance with yet another embodiment of the invention.

FIG. 10 illustrates an embodiment of a diaper 95, which may be an adult diaper (i.e., a "brief"), or a baby diaper, and which has notable differences relative to the conventional diaper 85 of FIG. 9. More specifically, the exemplary diaper 95 has a pair of lateral portions 96, similar in construction and/or materials to the lateral portions 86 of diaper 85 (FIG. 9). Notably, however, the lateral portions 96 of diaper 95 are free of elastic strands. Likewise, diaper 95 is free of standing leg barriers 92. The elastic strand-free and standing leg barrier-free design of diaper 95 is facilitated by virtue of the cupped configuration provided by a plurality of folds and corresponding bonds 100 in the lateral portions 96 of diaper 95. Obviation of the elastic strands and/or standing leg barriers may be desirable because it reduces the manufacturing complexity and the quantity and types of materials used in diaper 95.

Those of ordinary skill in the art will readily appreciate that, while FIG. 9 illustrates a diaper 95 that is free of elastic strands at the lateral portions 96, and free of standing leg barriers, the same features are applicable to other types of disposable absorbent product such as, and without limitation, training pants and pant-type diapers, which conventionally are known to include leg elastics and/or standing leg barriers. Further, while diaper 95 is free of elastic strands at the lateral portions 96, and also free of standing leg barriers, other embodiments are contemplated in which the lateral portions 96 are free of elastic strands but which, notwithstanding, include standing leg barriers or similar features to further enhance containment.

Exemplary embodiments of the invention are described as follows, in non-limiting fashion:

1. A disposable absorbent product extending along a longitudinal axis and a transverse axis orthogonal to said longitudinal axis, the disposable absorbent product comprising:
 a topsheet;
 a backsheet overlaying said topsheet, said topsheet and backsheet jointly defining first and second side edges of the disposable absorbent product on respective sides of said longitudinal axis;
 an absorbent core disposed between said topsheet and said backsheet for storing fluid secreted by the wearer of said disposable absorbent product, said absorbent core having first and second lateral edges respectively inboard of said first and second side edges of said disposable absorbent product so as to define respective first and second lateral portions of said disposable absorbent product free of said absorbent core;
 a plurality of folds parallel to said transverse axis; and
 a plurality of bonds in at least one of said first or second lateral portions securing said plurality of folds in place.

2. The disposable absorbent product of claim 1, wherein said bonds do not extend to said absorbent core.

3. The disposable absorbent product of either of claim 1 or 2, wherein at least two of said bonds are located along a common transverse line in said first and second lateral portions.

4. The disposable absorbent product of any of claims 1-3, wherein said first and second lateral edges of said absorbent core define a plurality of lateral depressions of said absorbent core at said folds.

5. The disposable absorbent product of any of claims 1-4, wherein said bonds are selected from the group consisting of adhesive bonds, ultrasonic bonds, infrared bonds, thermal bonds, and compression bonds.

6. The disposable absorbent product of any of claims 1-5, wherein said lateral portions are free of elastic strands.

7. The disposable absorbent product of any of claims 1-7, wherein said disposable absorbent product is in the form of a diaper, said diaper being free of standing leg barriers.

8. A method for making a disposable absorbent product including a topsheet, a backsheet, and an absorbent core disposed between the topsheet and backsheet, the topsheet and backsheet jointly defining first and second side edges of the disposable absorbent product on respective sides of a longitudinal axis of the disposable absorbent product, the method comprising:
 locating the absorbent core relative to the topsheet and backsheet so as to define respective first and second lateral portions of the disposable absorbent product free of absorbent core;
 forming a plurality of folds parallel to a transverse axis of the disposable absorbent product orthogonal to the longitudinal axis thereof; and
 bonding at least one of the first or second lateral portions at a plurality of the folds, so as to secure the folds in place.

9. The method of claim 8, wherein bonding at least one of the first or second lateral portions includes leaving the absorbent core free of bonds.

10. The method of either of claim 8 or 9, wherein bonding at least one of the first or second lateral portions includes forming an adhesive, ultrasonic, infrared, thermal, or compression bond at that first or second lateral portion.

11. The method of any of claims 8-10, further comprising:
 forming at least one fold spanning the first and second lateral portions and extending along a common line parallel to the transverse axis; and
 bonding the first and second lateral portions along the at least one fold.

Yet other embodiments are also contemplated for uses and methods for making disposable absorbent products according to any of claims 1 to 7, as described above.

From the above disclosure of the general principles of the present invention and the preceding detailed description of exemplary embodiments, those skilled in the art will readily comprehend the various modifications to which this invention is susceptible. Accordingly, this invention is intended to be limited only by the scope of the following claims and equivalents thereof.

What is claimed is:

1. A disposable absorbent product extending along a longitudinal axis, the disposable absorbent product comprising:
 a topsheet;
 a backsheet overlaying said topsheet, said topsheet and backsheet jointly defining first and second side edges of the disposable absorbent product on respective sides of said longitudinal axis;
 an absorbent core disposed between said topsheet and said backsheet for storing fluid secreted by the wearer of said disposable absorbent product, said absorbent core having first and second lateral edges respectively inboard of said first and second side edges of said disposable absorbent product so as to define respective first and second lateral portions of said disposable absorbent product free of said absorbent core;
 a plurality of folds in said first or second lateral portions transverse to the longitudinal axis, wherein the plurality of folds are made up of at least said backsheet and said topsheet and bring into contact adjacent segments of said first lateral portion or adjacent segments of said second lateral portion; and
 a plurality of bonds in at least one of said first or second lateral portions securing said adjacent segments of said first lateral portion to one another or said adjacent segments of said second lateral portion to one another.

2. The disposable absorbent product of claim 1, wherein said bonds do not extend to said absorbent core.

3. The disposable absorbent product of claim 1, wherein at least two of said bonds are located along a common transverse line in said first and second lateral portions.

4. The disposable absorbent product of claim 1, wherein said first and second lateral edges of said absorbent core define a plurality of notches of said absorbent core adjacent said folds.

5. The disposable absorbent product of claim 1, wherein said bonds are selected from the group consisting of adhesive bonds, ultrasonic bonds, infrared bonds, thermal bonds, and compression bonds.

6. The disposable absorbent product of claim 1, wherein said lateral portions are free of elastic strands.

7. The disposable absorbent product of claim 6, wherein said disposable absorbent product is in the form of a diaper, said diaper being free of standing leg barriers.

8. A disposable absorbent product extending along a longitudinal axis and a transverse axis orthogonal to said longitudinal axis, the disposable absorbent product comprising:
   a topsheet;
   a backsheet overlaying said topsheet, said topsheet and backsheet jointly defining first and second side edges of the disposable absorbent product on respective sides of said longitudinal axis;
   an absorbent core disposed between said topsheet and said backsheet for storing fluid secreted by the wearer of said disposable absorbent product, said absorbent core having first and second lateral edges respectively inboard of said first and second side edges of said disposable absorbent product so as to define respective first and second lateral portions of said disposable absorbent product free of said absorbent core;
   a plurality of folds parallel to said transverse axis, at least one of said folds spanning said first and second lateral portions, wherein the plurality of folds bring into contact adjacent segments of said first lateral portion or adjacent segments of said second lateral portion; and
   a plurality of bonds located along said folds and securing said adjacent segments of said first lateral portion to one another or said adjacent segments of said second lateral portion to one another.

9. The disposable absorbent product of claim 8, wherein said first and second lateral edges of said absorbent core define a plurality of notches of said absorbent core at each of said folds.

10. The disposable absorbent product of claim 8, wherein said lateral portions are free of elastic strands.

11. The disposable absorbent product of claim 10, wherein said disposable absorbent product is in the form of a diaper, said diaper being free of standing leg barriers.

12. The disposable absorbent product of claim 8, wherein said bonds include at least one of ultrasonic bonds, compression bonds, or thermal bonds.

13. A method for making a disposable absorbent product including a topsheet, a backsheet, and an absorbent core disposed between the topsheet and backsheet, the topsheet and backsheet jointly defining first and second side edges of the disposable absorbent product on respective sides of a longitudinal axis of the disposable absorbent product, the method comprising:
   locating the absorbent core relative to the topsheet and backsheet so as to define respective first and second lateral portions of the disposable absorbent product free of absorbent core;
   forming a plurality of folds transverse to the longitudinal axis of the disposable absorbent product to bring into contact adjacent segments of said first lateral portion or adjacent segments of said second lateral portion; and
   bonding each of said folds within at least one of the first or second lateral portions, so as to secure said adjacent segments of said first lateral portion to one another or said adjacent segments of said second lateral portion to one another.

14. The method of claim 13, wherein bonding each of said folds includes leaving the absorbent core free of bonds.

15. The method of claim 13, wherein bonding each of said folds includes forming an adhesive, ultrasonic, infrared, thermal, or compression bond at the at least one of the first or second lateral portions.

16. The method of claim 13, further comprising:
   forming at least one fold spanning the first and second lateral portions and extending along a common line orthogonal to the longitudinal axis; and
   bonding the first and second lateral portions along the at least one fold.

17. The disposable absorbent product of claim 1, wherein the disposable absorbent product further extends along a transverse axis orthogonal to the longitudinal axis, said plurality of folds being generally parallel to the transverse axis.

18. The disposable absorbent product of claim 1, wherein said bonds extend through said topsheet and said backsheet.

19. The disposable absorbent product of claim 8, wherein said bonds extend through said topsheet and said backsheet.

20. The method of claim 13, wherein forming a plurality of folds includes forming a plurality of folds orthogonal to the longitudinal axis of the disposable absorbent product.

* * * * *